United States Patent [19]

Rudd et al.

[11] Patent Number: 5,525,503

[45] Date of Patent: Jun. 11, 1996

[54] SIGNAL TRANSDUCTION VIA CD28

[75] Inventors: Christopher E. Rudd, Cambridge; Prasad Kanteti, Boston, both of Mass.

[73] Assignee: Dana-Farber Cancer Institute, Inc., Boston, Mass.

[21] Appl. No.: 128,971

[22] Filed: Sep. 28, 1993

[51] Int. Cl.$^6$ ................. C12N 5/00; C07K 5/00
[52] U.S. Cl. ...................... 435/240.2; 530/330
[58] Field of Search .................. 435/244, 240.2

[56] References Cited

U.S. PATENT DOCUMENTS 5,250,431  10/1993  Rudd et al. ............... 435/240.2

OTHER PUBLICATIONS

Aruffo et al., "Molecular cloning of a CD28 by a high-efficiency COS cell expression system", Proc. Natl. Acad. Sci USA 84:8573–8577 (1987).

Auger et al., "PDGF–Dependent Tyrosine Phosphorylation Stimulates Production of Novel Polyphosphoinositides in Intact Cells", Cell 57:167–175 (1989).

Cochet et al., "Interaction between the Epiderman Growth Factor Receptor and Phosphoinositide Kinases", J. Biol. Chem. 2266:637–644 (1991).

Fanti et al., "Distinct Phosphotyrosines on a Growth Factor Receptor Bind to a Specific Molecular That Mediate Different Signaling Pathways", Cell 69:413–423 (1992).

Linsley et al., "The Role of the CD28 Receptor During T Cell Responses to Antigen", Annu. Rev. Immunol. 11:191–212 (1993).

Lu et al., "CD28–Induced T Cell Activation–Evidence for a Protein–Tyrosine Kinase Signal Transduction Pathway", J. Immunol. 149:24–29 (1992).

Pawson et al., "SH2 and SH3 Domains: From Structure to Function", Cell 71:359–362 (1992).

Perlmutter et al., "Regulation of Lymphocyte Function by Protein Phosphorylation", Annu. Rev. Immunol. 11:451–99 (1993).

Prasad et al., "Src–homology 3 domain of protein kinase p.59$^{fyn}$ mediates binding to phosphatidylinositol 3–kinase in T cells", Proc. Natl. Acad. Sci. USA 90:7366–7370 (1993).

Songyang et al., "SH2 Domains Recongnize Specific Phosphopeptide Sequences", Cell 72:767–778 (1993).

Whitman et al., "Type I phosphatidylinositol kinase mades a novel inositol phospholipid, phosphatidylinositol–3–phosphate", Nature 332:644–646 (1988).

Baker et al., "Phosphatidylinositol 3'–kinase is Activated by Association with IRS–1 During Insulin Stimulation", The EMBO Journal 11:3469–3479, 1992.

Bjorge et al., "Activated Type I Phosphatidylinositol Kinase is Associated with the Epidermal Growth Factor (EGF) Receptor Following EGF Stimulation", Proc. Natl. Acad. Sci USA 87:3816–3820, 1990.

Kashishian et al., "Phosphorylation Site in the PDGF Receptor with Different Specificities for Binding GAP and P13 Kinase In Vivo," The EMBO Journal 11:1373–1382, 1992.

Lev. et al., "Interkinase Domain of Kit Contains the Binding Site for Phosphatidylinositol 3'Kinase", Proc. Natl. Acad. Sci. USA 89:678–682, 1992.

Tuveson et al., "CD19 of B Cells as a Surrogate Kinase Insert Region to Bind Phosphatidylinositol 3–Kinase", Science 260:986–989, 1993.

White et al., "Insulin Rapidly Stimulates Tyrosins Phosphorylation of a M–185,000 Protein in Intact Cells", Nature 318:183–186, 1985.

Whitman et al., "Type I Phosphattidylinositol Kinase Makes a Novel Inositol Phospholipid, Phosphatidylinositol–3–phosphate", Nature 332:644–646, 1988.

Aruffs et al PNAS 84:8573, 1987.

Fontl et al Cell 69:413, 1992.

*Primary Examiner*—Suzanne E. Ziska
*Attorney, Agent, or Firm*—Fish & Richardson

[57] ABSTRACT

Disclosed are compositions and methods of blocking T cell signal transduction by introducing into a T cell a peptide comprising a PI 3-kinase-binding-sequence which decreases the association of PI 3-kinase with CD28. Also disclosed are compositions and methods of amplifying T cell activation by introducing into a T cell, a plurality of modified T cell surface proteins, the cytoplasmic tail of which comprises a plurality of copies of a PI 3-kinase-binding-sequence.

2 Claims, 7 Drawing Sheets

5,525,503

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( x i ) SEQUENCE DESCRIPTION: SEQ ID NO: 1:

Tyr  Met  Xaa  Met
 1

( 2 ) INFORMATION FOR SEQ ID NO: 2:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 2:

Leu  His  Ser  Asp  Tyr  Met  Asn  Met  Thr  Pro  Arg  Arg  Pro
 1                          5                                  10

( 2 ) INFORMATION FOR SEQ ID NO: 3:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 3:

Ser  Asp  Gly  Gly  Tyr  Met  Asp  Met  Ser  Lys  Asp  Glu  Ser
 1                          5                                  10

( 2 ) INFORMATION FOR SEQ ID NO: 4:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( x i ) SEQUENCE DESCRIPTION: SEQ ID NO: 4:

Gly  Val  Asp  Thr  Tyr  Val  Glu  Met  Arg  Pro
 1                          5                              10

( 2 ) INFORMATION FOR SEQ ID NO: 5:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( x i ) SEQUENCE DESCRIPTION: SEQ ID NO: 5:

Ser  Thr  Asn  Glu  Tyr  Met  Asp  Met  Lys  Pro (2) INFORMATION FOR SEQ ID NO: 6:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 6:

Asp Asp Gly Tyr Met Pro Met Ser Pro Gly Val
1               5                   10

(2) INFORMATION FOR SEQ ID NO: 7:

(i) SEQUENCE CHARACTERISTICS:
        (A) LENGTH: 12
        (B) TYPE: amino acid
        (C) STRANDEDNESS:
        (D) TOPOLOGY: linear (xi) SEQUENCE DESCRIPTION: SEQ ID NO: 7:

Gly Asn Gly Asp Tyr Met Pro Met Ser Pro Lys Ser
1               5                   10

(2) INFORMATION FOR SEQ ID NO: 8:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 8:

Pro Asn Gly Tyr Met Met Met Ser Pro Ser Gly
1               5                   10

(2) INFORMATION FOR SEQ ID NO: 9:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 9:

Thr Gly Asp Tyr Met Asn Met Ser Pro Val Gly
1               5                   10

(2) INFORMATION FOR SEQ ID NO: 10:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 10:

Ser Glu Glu Tyr Met Asn Met Asp Leu Gly Pro
1               5                   10

(2) INFORMATION FOR SEQ ID NO: 11:

(i) SEQUENCE CHARACTERISTICS:
        (A) LENGTH: 12
        (B) TYPE: amino acid
        (C) STRANDEDNESS:
        (D) TOPOLOGY: linear ( x i ) SEQUENCE DESCRIPTION: SEQ ID NO: 11:

Glu Glu Glu Tyr Met Pro Met Glu Asp Leu Tyr Leu
 1               5                       10

( 2 ) INFORMATION FOR SEQ ID NO: 12:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 12:

Asp Ala Asp Glu Tyr Leu Ile Pro Gln Gln Gly Phe Phe
 1               5                       10

( 2 ) INFORMATION FOR SEQ ID NO: 13:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 13:

Ser Asn Gln Glu Tyr Leu Asp Leu Ser Met Pro Leu Asp
 1               5                       10

( 2 ) INFORMATION FOR SEQ ID NO: 14:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 14:

Glu Glu Glu Tyr Met Pro Met Glu Asp Leu Tyr Leu
 1               5                       10

( 2 ) INFORMATION FOR SEQ ID NO: 15:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( x i ) SEQUENCE DESCRIPTION: SEQ ID NO: 15:

His Ser Asp Tyr Met Asn Met Thr Pro Arg Arg
 1               5                       10

( 2 ) INFORMATION FOR SEQ ID NO: 16:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( x i ) SEQUENCE DESCRIPTION: SEQ ID NO: 16:

Tyr Met Asn Met
 1

( 2 ) INFORMATION FOR SEQ ID NO: 17:

( i ) SEQUENCE CHARACTERISTICS:

(A) LENGTH: 4
(B) TYPE: amino acid
(C) STRANDEDNESS:
(D) TOPOLOGY: linear (xi) SEQUENCE DESCRIPTION: SEQ ID NO: 17:

Tyr Met Asp Met
 1

(2) INFORMATION FOR SEQ ID NO: 18:

(i) SEQUENCE CHARACTERISTICS:
(A) LENGTH: 4
(B) TYPE: amino acid
(C) STRANDEDNESS:
(D) TOPOLOGY: linear (xi) SEQUENCE DESCRIPTION: SEQ ID NO: 18:

Tyr Val Glu Met
 1

(2) INFORMATION FOR SEQ ID NO: 19:

(i) SEQUENCE CHARACTERISTICS:
(A) LENGTH: 4
(B) TYPE: amino acid
(C) STRANDEDNESS:
(D) TOPOLOGY: linear (xi) SEQUENCE DESCRIPTION: SEQ ID NO: 19:

Tyr Met Pro Met
 1

(2) INFORMATION FOR SEQ ID NO: 20:

(i) SEQUENCE CHARACTERISTICS:
(A) LENGTH: 4
(B) TYPE: amino acid
(C) STRANDEDNESS:
(D) TOPOLOGY: linear (xi) SEQUENCE DESCRIPTION: SEQ ID NO: 20:

Tyr Leu Ile Pro
 1

(2) INFORMATION FOR SEQ ID NO: 21:

(i) SEQUENCE CHARACTERISTICS:
(A) LENGTH: 4
(B) TYPE: amino acid
(C) STRANDEDNESS:
(D) TOPOLOGY: linear (xi) SEQUENCE DESCRIPTION: SEQ ID NO: 21:

Tyr Leu Asp Leu
 1

SIGNAL TRANSDUCTION VIA CD28

This invention was made with Government support under grant no. CA51887-02 awarded by the National Cancer Institute as well as grant nos. GM41890 and GM36624 from the National Institutes of Health. The Government has certain rights in the invention.

FIELD OF THE INVENTION

This invention relates to signal transduction in T cells.

BACKGROUND OF THE INVENTION

T-cell activation involves a two-step process: an antigen-specific signal generated by the TcRζ/CD3 complex, followed by a second signal delivered by an accessory cell (June et al., 1990, Immunol. Today 11:211). The TcRζ/CD3 complex defines the specificity of recognition, while the co-stimulatory signal is thought to regulate lymphokine expression and proliferation (Mueller et al., 1989, Ann. Rev. Immunol. 7:445; Kohno et al., 1990, Cell. Immunol. 131:1). Engagement of the antigen-receptor in the absence of the co-stimulatory receptor results in clonal non-responsiveness or anergy.

CD28, a disulfide-linked homodimer of 44 kDa expressed on the surface of thymocytes and the majority of T cells (Hara et al., 1985, J. Exp. Med. 161:1513; Moretta et al., 1985, J. Exp Med. 162: 823), is an essential second signal in T cell activation. CD28 is expressed on CD4+ and CD8+ T cells and also on CD4+CD8+ thymocytes (Martin et al., 1986, J. Immunol. 136:3282). Structurally, CD28 is comprised of a single immunoglobulin-like domain and a 51 amino acid cytoplasmic tail (Aruffo and Seed, 1987, Proc. Natl. Acad. Sci. USA 84:8573, herein incorporated by reference). Activation of CD28+ T cells by suboptimal levels of antigen together with anti-TcRζ/CD3 and anti-CD2 is augmented by anti-CD28 as measured by proliferation and lymphokine production (June et al., 1987, Mol. Cell Bio 7:4472; Martin et al., 1986, J. Immunol. 136: 3282; Yang et al., 1988, J. Exp. Med. 168:1457; van Lier et al., 1988, Eur. J. Immunol. 18:1753). Binding of antibody to CD28 in the presence of phorbol ester induces mitogenesis (Hara et al., supra), and CD28 signalling initially stabilizes mRNA for various lymphokines, followed by an increase in transcription (Lindsten et al., 1989, Science 244:339).

The natural ligand for CD28 has been identified as B7/BB1 (Linsley et al., 1990, Proc. Natl. Acad. Sci. USA 87:5031). B7 is a surface glycoprotein that is expressed on activated B cells and interferon-γ treated monocytes (Freeman et al., 1989, J. Immunol. 143:2714; Yockochi et al., 1982, J. Immunol. 128 823; Freedman et al., 1991, Cell. Immunol. 137:429). The binding of B7/BB1 to CD28 potentiates the level of proliferation initiated by the antigen receptor complex (Koulova et al., 1991, J. Exp. Med. 173:759; Linsley; Gimmi et al., 1991, Proc. Natl. Acad. Sci. USA 88:6575). Similarly, the inability of fixed accessory cells to induce T-cell response can be corrected by ligation of CD28 with allogeneic accessory cells or antibody (Jenkins et al., 1988, J. Immunol. 140:3324; Harding). Engagement of the TcRζ/CD3 complex in the absence of CD28 ligation leads to a state of anergy. The requirement for this second signal may play an important role in vivo in establishing tolerance in the T-cell periphery to antigens that were not encountered in the thymus.

SUMMARY OF THE INVENTION

The biochemical nature of the second signal for T cell activation has been a fundamental and long-standing question. Disclosed herein is an elucidation of this second signal as a novel signalling pathway in which CD28 is coupled directly to PI 3 kinase, a lipid kinase that phosphorylates the D-3 position of the inositol ring of phosphatidylinositol, phosphatidylinositol 4-phosphate and phosphatidylinositol 4,5 bisphosphate, generating PI 3-P, PI 3,4-$P_2$ and PI 3,4, 5-$P_3$. The coupling of CD28 to PI 3-kinase potentiates the second signal leading to T cell activation. The invention provides methods for modulating T cell activation utilizing this pathway.

The invention features a method of modulating signal transduction in T cells by introducing into a T cell a peptide comprising a PI 3-kinase-binding fragment of the cytoplasmic tail of CD28, thereby decreasing the association of PI 3-kinase with CD28. In one embodiment, the peptide comprises Tyr-Met-X-Met (SEQ ID NO:1), in which the tyrosine residue of the peptide is phosphorylated and "X" represents any amino acid, preferably asparagine, aspartic acid, glutamic acid or methionine.

A peptide useful for blocking the interaction of PI 3-kinase with CD28 will ordinarily be at least about 4 amino acids, usually about 10 contiguous amino acids, preferably at least 20 contiguous amino acids, and most preferably at least 40 or 50 amino acids in length.

In another aspect, the invention features a modified CD28 molecule lacking a portion of the cytoplasmic tail of wild type CD28, which portion contains at least part of SEQ ID NO:1. In preferred embodiments, the modified CD28 includes essentially all of the wild type CD28 except up to 51 residues of the cytoplasmic tail. More preferably, only up to 40 amino acid residues of the tail are deleted, and even more preferably, only up to 30 amino acid residues. Most preferably, between 1 and 20 are deleted (e.g., up to 10).

In another aspect, the invention provides a modified CD28 molecule containing a mutation in the cytoplasmic tail of wild type CD28, wherein at least one residue of SEQ ID NO:1 is mutated (i.e., is deleted or replaced with a different residue, preferably representing a non-conservative change). A DNA encoding such a molecule, and a cell expressing the DNA, are also within the invention.

The invention also includes a modified T cell surface protein containing a cytoplasmic tail comprising a plurality of copies (e.g., 2–10) of a PI-3 kinase binding sequence. In a preferred embodiment, the PI 3-kinase binding sequence comprises SEQ ID NO:1. In another embodiment, the PI 3-kinase binding sequence is Tyr-Met-Asn-Met (SEQ ID NO: 16), Tyr-Met-Asp-Met (SEQ ID NO:17), Tyr-Val-Glu-Met (SEQ ID NO:18), Tyr-Met-Pro-Met (SEQ ID NO:19), Tyr-Leu-Ile-Pro (SEQ ID NO:20) or Tyr-Leu-Asp-Leu (SEQ ID NO:21). In another embodiment, the protein is CD28 modified to comprise a plurality of copies of SEQ ID NO:1 in its cytoplasmic tail. The modified T cell surface protein may alternatively be CD2, CD3, CD7, CTLA-4, LFA-1, CD18, CD5, CD4, or CD8. A DNA encoding such a modified T cell surface protein and a cell which expresses the DNA are also within the invention.

In another aspect, the invention features a method of amplifying signal transduction in a T cell, comprising introducing into the cell a plurality of molecules of the modified cell-surface protein comprising a plurality of copies of a PI-3 kinase binding sequence, and crosslinking at least two of such proteins.

Another aspect of the invention features a method for screening candidate compounds to identify a compound capable of modulating the association of CD28 with PI 3-kinase by contacting a cell that expresses CD28 and PI 3-kinase with a candidate compound, immunoprecipitating CD28, and determining the amount or activity of PI 3-kinase in the immunoprecipitate, wherein a decrease in the amount or activity in the presence of the candidate compound, compared to the amount or activity in the absence of the candidate compound, is an indication that the candidate compound inhibits the association of PI 3-kinase with CD28, while an increase in the amount or activity of PI 3-kinase in the presence of the candidate compound, compared to the amount or activity in the absence of the candidate compound, is an indication that the candidate compound enhances the association of PI 3-kinase with CD28.

Also provided is a method for screening candidate compounds to identify a compound capable of modulating the association of CD28 with PI 3-kinase by contacting a cell that expresses CD28 and PI 3-kinase with a candidate compound, immunoprecipitating PI 3-kinase, and determining the amount of CD28 in the immunoprecipitate, wherein a decrease in the amount of CD28 in the presence of the candidate compound, compared to the amount in the absence of the candidate compound, is an indication that the candidate compound inhibits the association of PI 3-kinase with CD28, while an increase in the amount in the presence of the candidate compound, compared to the amount in the absence of the candidate compound, is an indication that the candidate compound enhances the association of PI 3-kinase with CD28.

The PI 3-kinase enzyme has two subunits, a p110 catalytic subunit coupled to an adapter p85 subunit, to which CD28 has been shown to bind. Yet another aspect of the invention provides a method for screening candidate compounds to identify a compound capable of modulating the association of CD28 with PI 3-kinase by providing CD28 and the p85 subunit of PI 3-kinase in the presence and absence of a candidate compound and determining the resulting amount of CD28/p85 complex, wherein a decrease in the amount in the presence of the compound compared to the amount in the absence of the compound is an indication that the candidate compound inhibits the association of PI 3-kinase with CD28, while an increase in the amount in the presence of the compound compared to the amount in the absence of the compound is an indication that the candidate compound enhances the association of PI 3-kinase with CD28.

In a final aspect, the invention features a transgenic non-human mammal harboring a transgene encoding a T cell surface protein having a cytoplasmic tail that contains a plurality of copies of a PI-3 kinase-binding amino acid sequence. In preferred embodiments, the mammal is a mouse, rat, rabbit, cow, pig, sheep or goat; the surface protein is CD28 or CD3; and the PI 3-kinase-binding sequence comprises SEQ ID NO:1.

"Transgenic" as used herein means a mammal the nucleated cells of which include a DNA sequence which is inserted by artifice into a cell and becomes a part of the genome of the animal which develops from that cell. Such a transgene may be partly or entirely heterologous to the transgenic animal.

DETAILED DESCRIPTION

Reagents

Figure 1:
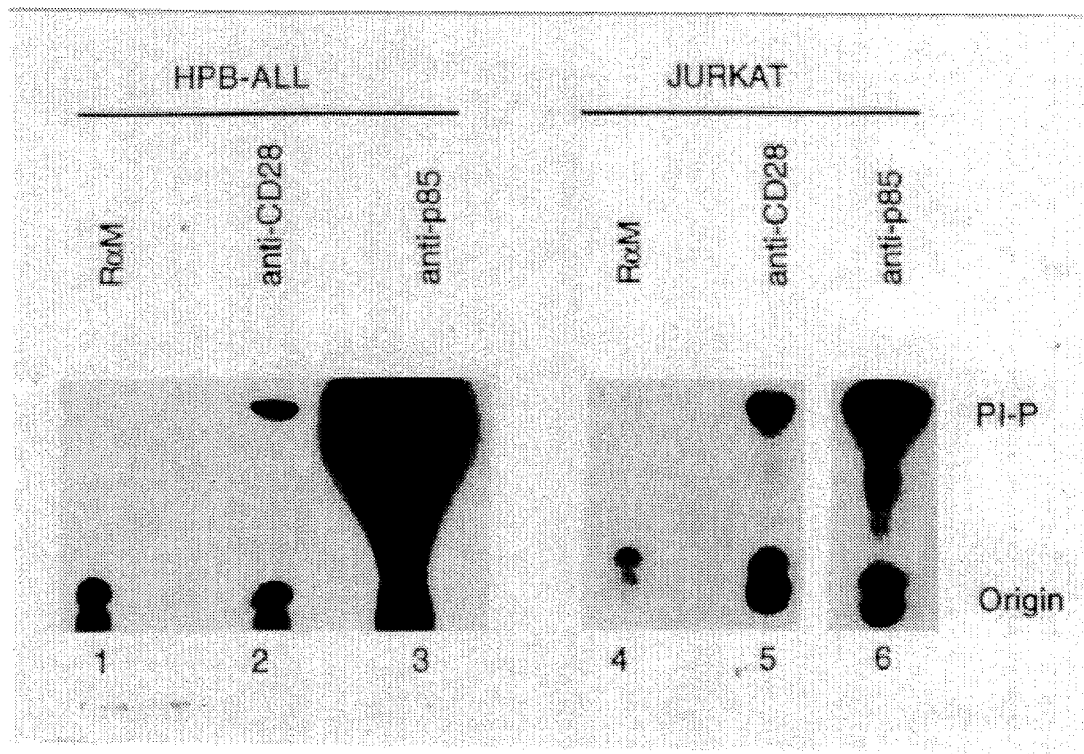
FIG. 1 is a photograph of a thin layer chromatographic (TLC) analysis of lipids generated by a CD28-associated lipid kinase. Immunoprecipitations were conducted from Nonidet P-40 cell lysates from HPB-ALL (lanes 1–3) and Jurkat cells (lanes 4–6). The following antibodies were used: rabbit anti-mouse (RαM) (lane 1, 4); anti-CD28 (lane 2,5) and anti-p85 of PI 3-kinase (lane 3,6).

The following reagents are widely available. Nonidet P-40, phenyl methyl sulfonyl fluoride (PMSF) (Sigma, St. Louis, Mo.), sodium dodecyl sulfate (SDS), acrylamide and bisacrylamide (National Diagnostics, Manville, N.J.), Protein A Sepharose beads, Ficoll-Paque (Pharmacia, N.J.), phosphatidyl inositol, γ-32P-ATP (specific activity, 3000 Ci/mmol) (NEN, Mass.). Aluminum backed precoated silica gel plates (E. Merck, Germany).

Antibodies

Monoclonal antibodies were employed which are specific for CD28: (9.3) (Becton Dickinson, Calif.), and 4B10; and for CD29:4B4 (Coulter Immunology, Hialeah, Fla.). Also utilized were anti-p85 PI 3-kinase antisera (Transduction Laboratories, Lexington, Ky.) and RαM immunoglobulin (Dako Corporation, Carpinteria, Calif.).

Cells

T lymphoblastoid cell lines, e.g., Jurkat (ATCC TIB 152) were cultured in RPMI-1640 containing 10% (v/v) fetal bovine serum, L-glutamine (2 mM), penicillin (50 U/ml) and streptomycin (50 mg/ml) at 37° C and 5% $CO_2$.

Immunoprecipitation

Cells were lysed in ice cold NP-40 [0.5% (v/v)], 20 mM Tris HCl at pH 8.3, containing 150 mM NaCl, 1 mM PMSF and the lysate incubated with various antibodies, as described in Prasad et al., 1993, Proc. Natl. Acad. Sci. USA 90:7366, herein incorporated by reference. Immune complexes were washed thrice with the lysis buffer; thrice with 100 mM Tris at pH 7.5 containing 0.5 M LiCl (Tris/LiCl); and twice with TNE (10 mM Tris-HCl, pH 7.5, 150 mM NaCl and 1 mM EGTA).

Crosslinking of surface receptors

For receptor-crosslinking experiments, HPB-ALL cells were suspended at a density of $20 \times 10^6$ cells/ml in ice cold RPMI containing fetal calf serum (FCS) (2% v/v) and were incubated with an excess of anti-CD3 antibody for one hour at 4° C. washed and further incubated for 30 min with RαM (1 mg/ml). Cells were then re-suspended in warm RPMI and incubated at 37° C. for 3 min. RαM alone served as a negative control.

GST fyn-SH2, SH3, SH2/SH3 Fusion Proteins

Glutathione-S-transferase (GST) fusion proteins were generated as previously described (Prasad et al, supra). Briefly, DNA sequences encoding the SH2 (residues 149–257), SH3 (82–148) and SH2/SH3 (82–257) domains of fyn tyrosine kinase were amplified by the Polymerase Chain Reaction (PCR) from a plasmid containing full length fyn cDNA and subcloned into the pGEX-2T vector (Pharmacia, Uppsala, Sweden). Competent E. coli DH5α bacteria were used for transformation and expression of the fusion proteins. HPB-ALL cell lysates were prepared and incubated with the GST and GST fusion proteins (1.1 nmoles/ml of lysate) in the presence of fatty acid-free bovine serum albumin (BSA) (1.0 mg/ml) for one hour at 4° C. Then 100 ml of a 50% suspension of Glutathione Sepharose beads (Pharmacia, Uppsala, Sweden) were incubated for 10–15 min with the lysate. Following extensive washes (3× with lysis buffer, 3× Tris/LiCl and 2× TNE), the complexes were incubated with sonicated PI and γ32P-ATP. Reaction products were separated on TLC and the PI-P spots were visualized by autoradiography. TLC spots were extracted, deacylated and analyzed in a Beckman HPLC system using an ion exchange column as described in Prasad et al. supra, and Whitman et al, 1988, Nature, 332:644, all of which are incorporated by reference.

Baculovirus Expression System cDNA encoding full-length human fyn (Cooke et al., 1989, New Biologist 1:66–74) and the p85 subunit of PI 3-kinase was amplified by the PCR (Escobedo et al., 1991, Cell 65:75–82; Skolnick et al., 1991, Cell 65:83–90; Otsu et al., 1991, Cell 65:91–104) and cloned into the transfer vector pvl1393 (InvitroGen, San Diego, Calif.) into the Bam H1 site. Sf21 cells (InvitroGen Corp., San Diego, Calif.) were then transfected with a mixture of linear wild type baculoviral DNA (InvitroGen, San Diego, Calif.) and pVL1393-DNA constructs, and screened for recombinant virus plaques of the occlusion negative phenotype. Recombinant virus was purified from contaminating wild type virus by two rounds of plaque purification. The cells were infected with wild type or recombinant virus (multiplicity of infection=5), harvested 3 days later, and lysed in a solution of 1% Triton X-100 and 1 mM PMSF. Immunoprecipitations were carried out as described above. Following SDS-PAGE, proteins were transferred to a nitrocellulose membrane, blocked with gelatin (1% w/v), immunoblotted with anti-p85 rabbit serum (1:1000), and detected using goat anti-rabbit alkaline phosphatase, nitroblue tetrazolium (NBT) and 5-bromo-4-chloro-3-indolyl phosphate (BCIP) (Promega, Madison, Wis.).

Phosphatidyl inositol lipid kinase assay

The lipid kinase reaction was carried out on beads using soybean phosphatidyl inositol liposomes and γ32P-ATP (20 μCi). Lipids were then extracted using chloroform and methanol (1:1) and separated by thin layer chromatography on a silica gel plate precoated with potassium oxalate using a basic system (chloroform, methanol, water, ammonium hydroxide (60:47:11.3:2), as described in Whitman et al., supra and Auger et al., supra. The corresponding TLC spots were cut, counted for Cherenkov counts and extracted with a solution containing methylamine, methanol and n-butanol (57.7 ml of 25% methylamine in water, 61.6 ml of methanol and 15.6 ml of n-butanol) for 1 h at 53° C. This method also results in the deacylation of lipids. The samples were dried under vacuum and reconstituted in water. The non-deacylated lipids were removed by extracting twice with a mixture of n-butanol, light petroleum ether and ethylformate (20:4:1 vol/vol). The deacylated phospholipids were analyzed on a Beckman HPLC system using an ion exchange column and a gradient of $NH_4HPO_4$. $^3H$-PI-4P and adenosine diphosphate were used as internal standards.

Site-directed mutagenesis

Amino acid residues at positions Tyr-191, Met-194 and Tyr-209 were mutated using a site-directed mutagenesis system from Promega (Madison, Wis.). Briefly, the 1.5 kb HindIII/PstI fragment derived from a πH3M expression vector was inserted into a pS⁻ vector. Mutated oligonucleotides were annealed with the CD28 pS⁻ plasmid together with an ampicillin repair oligonucleotide. The plasmids were transformed into a repair-deficient strain, BMH 71-18, and were selected for ampicillin-resistant colonies. Mutations were identified by dideoxy sequence analysis. The 1.5 kb fragments containing single mutations were then subcloned into a πH3M vector. These three mutants and the DNA encoding the wild type CD28 were transfected into Cos-1 cells (ATCC CRL 1650) according to methods well known in the art. The transfected cells were incubated in DMEM tissue culture media supplemented with 10% FCS at 37° C. for 3 days. Cells were assessed for cell surface expression of CD28 by fluorescence-activated cell sorting (FACS) (EPICS, Coulter Immunology, Hialeah, Fla.).

Peptide Competition

Residues 191 to 194 within the cytoplasmic tail of CD28 correspond to the motif, Tyr-Met-X-Met, with a phosphorylated Tyr residue (Songyang et al., 1993, Cell 72:767). This sequence constitutes the optimal motif for binding of the first SH2 domain within the p85 subunit of PI 3-kinase. It is also found in a variety of other non-T cell receptors (PDGF-R, CSF-1, c-KIT) and intracellular binding proteins (insulin receptor substrate-1 (IRS-1), Polyoma Middle T antigen), as shown in Table 1. Each of these receptors has been found to bind to PI 3-kinase by means of the Tyr-Met-X-Met motif (Sun et al., 1991, Nature 318:183; Lev et al., Proc. Natl. Acad. Sci. USA 89:678; Girogetti et al, J. Biol. Chem. 268:7328; Bjorge et al., 1990, Proc. Natl. Acad. Sci. USA 87:3816; Backer et al., 1992, The EMBO J. 11:3469; Kashinshian et al.,1992, The EMBO J. 11:1373; Tuveson et al., Science 260:986.

The following peptides were used in peptide competition experiments: Polyoma virus middle T antigen-derived peptide, Glu-Glu-Glu-Tyr-Met-Pro-Met-Glu-Asp-Leu-Tyr-Leu (SEQ ID NO:14), either unphosphorylated or phosphorylated on the first Tyr residue; and the CD28derived peptide, His-Ser-Asp-Tyr-Met-Asn-Met-Thr-Pro-Arg-Arg (SEQ ID NO:15), either unphosphorylated or phosphorylated on the Tyr residue.

In peptide competition experiments, Jurkat cells (100× 10⁶) were lysed in 1 ml of NP-40 based lysis buffer and incubated with various concentrations of peptide for 2 hours at 4° C. prior to immunoprecipitation with anti-CD28 antibodies.

Immunoprecipitation of CD28

Anti-CD28 immunoprecipitates from T cells possess high levels of PI 3-kinase activity, as assessed by thin layer chromatography and HPLC analysis. Further, CD28 ligation, and to a lesser extent, TcRζ/CD3 ligation, resulted in a significant increase in the level of CD28associated PI 3-kinase activity. Concordantly, CD28 ligation over a 5 to 10 min period resulted in a dramatic increase in the association of PI 3-kinase with the receptor, as detected by anti-p85 PI 3-kinase immunoblotting. Furthermore, re-constitution experiments using baculoviral purified p85 demonstrated direct binding to CD28. An examination of the cytoplasmic tail of CD28 revealed the presence of the sequence, Tyr-Met-Asn-Met (SEQ ID NO:16) which fits the consensus sequence SEQ ID NO:1, which is the optimal site for PI 3-kinase binding. Peptide competition studies further revealed that PI 3-kinase binds to this motif, suggesting that the role of CD28 in determining states of anergy and peripheral tolerance in T cells may be mediated by PI 3-kinase.

Figure 2:
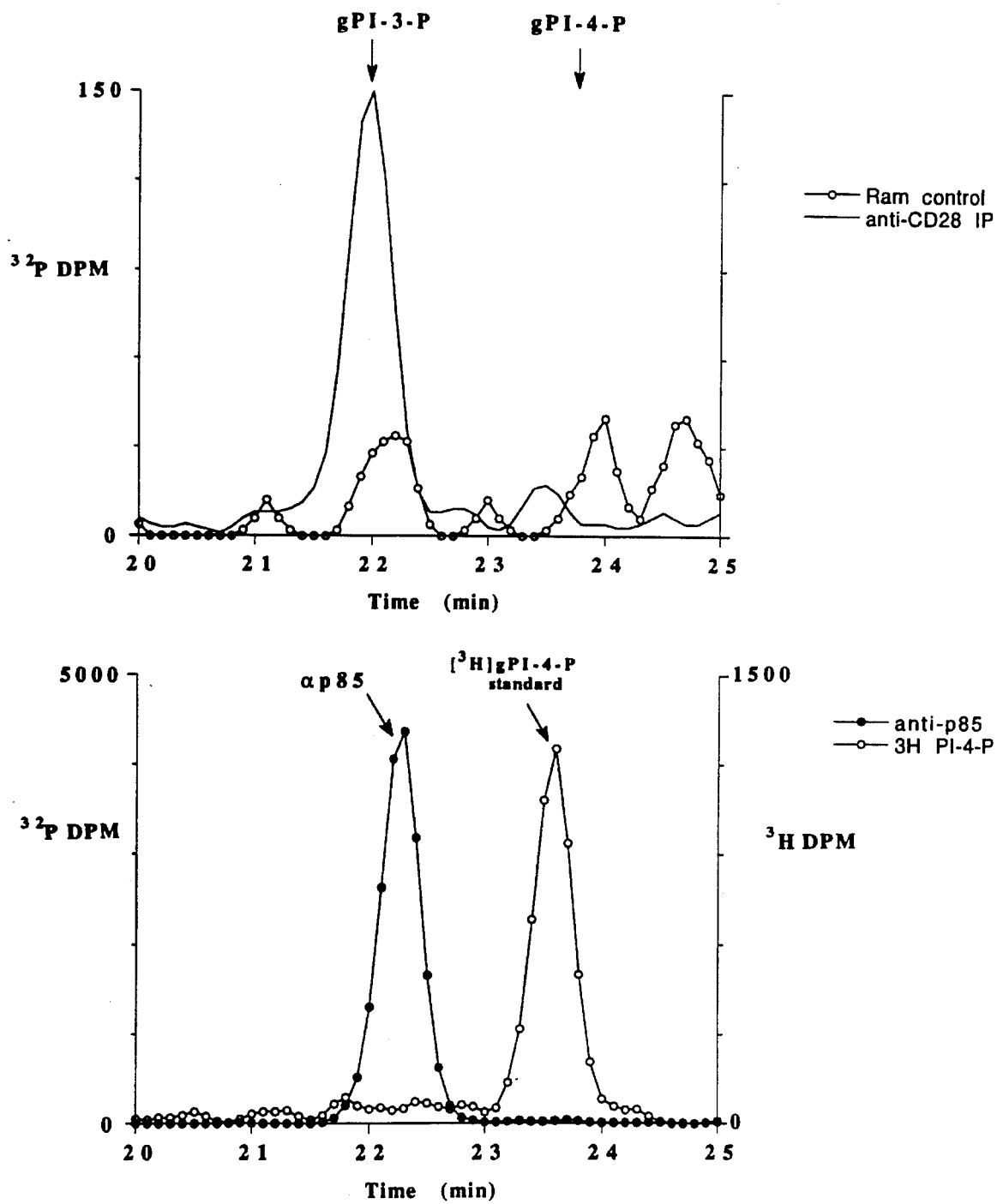
FIG. 2 is a graph showing high pressure liquid chromatography (HPLC) analysis of lipid products. Phosphorylated phosphatidyl inositol (PI-P) spots were extracted from TLC, deacylated and subjected to HPLC analysis. The upper panel shows that PI-P generated in generated in anti-CD28 precipitates consisted primarily of phosphorylated PI 3 (PI 3-P) (–). The negative control used was rabbit anti-mouse antibody (o—o). The lower panel shows p85 as a positive control for PI 3-P (●—●), while $^3$H-PI-4P was added as an internal standard (o—o).

Initially, CD28 was precipitated from HPB-ALL and Jurkat cell lysates and assessed for the presence of lipid kinase activity. As shown in FIG. 1, anti-CD28 precipitated significant amounts of PI 3-kinase activity from both HPB-ALL and Jurkat cells, as detected by thin layer chromatography (FIG. 1, lanes 2 and 5, respectively). Precipitates using antiserum against the p85 subunit of PI-3 kinase served as a positive control (lanes 3 and 6). Rabbit anti-mouse (lanes 1 and 4) or anti-CD29 precipitates served as a negative control. In order to identify the nature of the precipitated lipid kinase, the corresponding PI-P spots from the TLC plate were extracted, deacylated and subjected to HPLC analysis. Chromatographic separation of anti-CD28 precipitated material showed the presence of a major peak that corresponded to PI-3-P, indicating that the lipid kinase was PI 3-kinase (FIG. 2).

Figure 3:
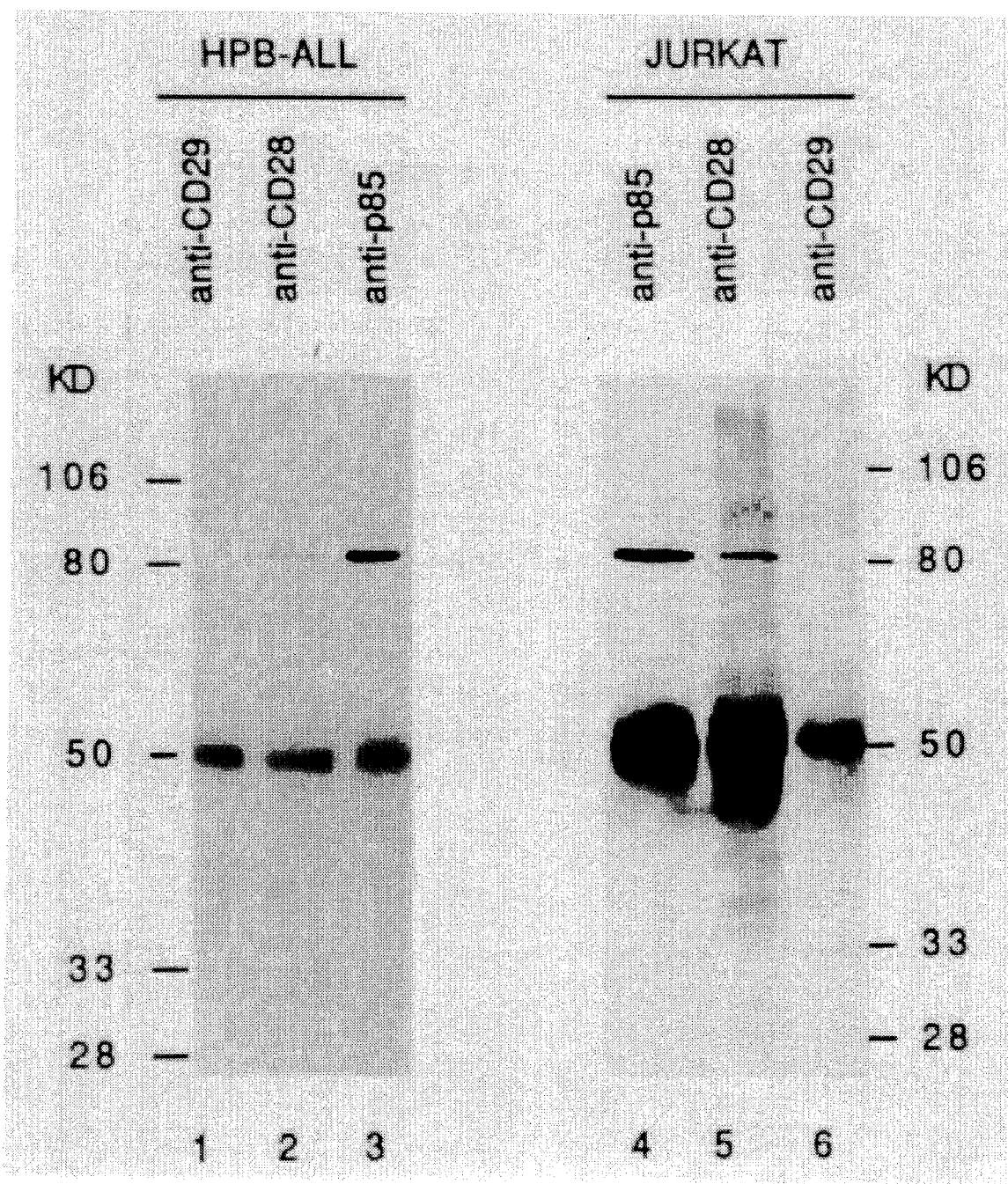
FIG. 3 is a photograph of an immunoblot assay which shows CD28 binding of the PI 3-kinase p85 subunit from the baculoviral expression system. *Spodoptera frugiperda* cells (Sf21) cells were infected with PI 3-kinase p85 (α isoform), and lysed in 1% Nonidet P-40. Sf21 lysates were then mixed with lysates from the HPB-ALL (lanes 1–3) or Jurkat cells (lanes 4–6), incubated for 2 hours, and subjected to immunoprecipitation with anti-CD29 antibody (lanes 1 and 6), anti-CD28 antibody (lanes 2 and 5), or anti-p85 antibody (lanes 3 and 4). Precipitates were separated by SDS-PAGE and immunoblotted with anti-p85 antisera.

Further confirmation of CD28-PI 3-kinase binding was obtained by reconstituting the interaction between purified PI 3-kinase and CD28 from T-cell lysates. PI 3-kinase is comprised of two subunits, an adapter p85 subunit coupled to a p110 catalytic subunit. Cell lysates from Sf21 insect cells expressing recombinant p85 were combined with CD28-containing T cell lysates, and subjected to immunoprecipitation. Under these conditions, anti-CD28 specifically precipitated the p85 subunit as detected by anti-p85 immunoblotting (FIG. 3, lanes 1–6). Immunoprecipitation of CD28 from both HPB-ALL and Jurkat cells revealed that CD28 bound to baculoviral-expressed p85 (lanes 2 and 5, respectively). As a positive control, anti-p85 precipitated the same 85 kDa band (lanes 3 and 6). As a negative control, anti-CD29 antibody was used to precipitate CD29 from the same cells, revealing that CD29 failed to associate with p85 (lanes 1 and 4). Similarly, control experiments using Sf21 insect cells alone failed to show CD28-associated material. These data indicate that CD28 binds directly to the p85 subunit without the need for the p110 subunit of PI 3-kinase.

Figure 4:
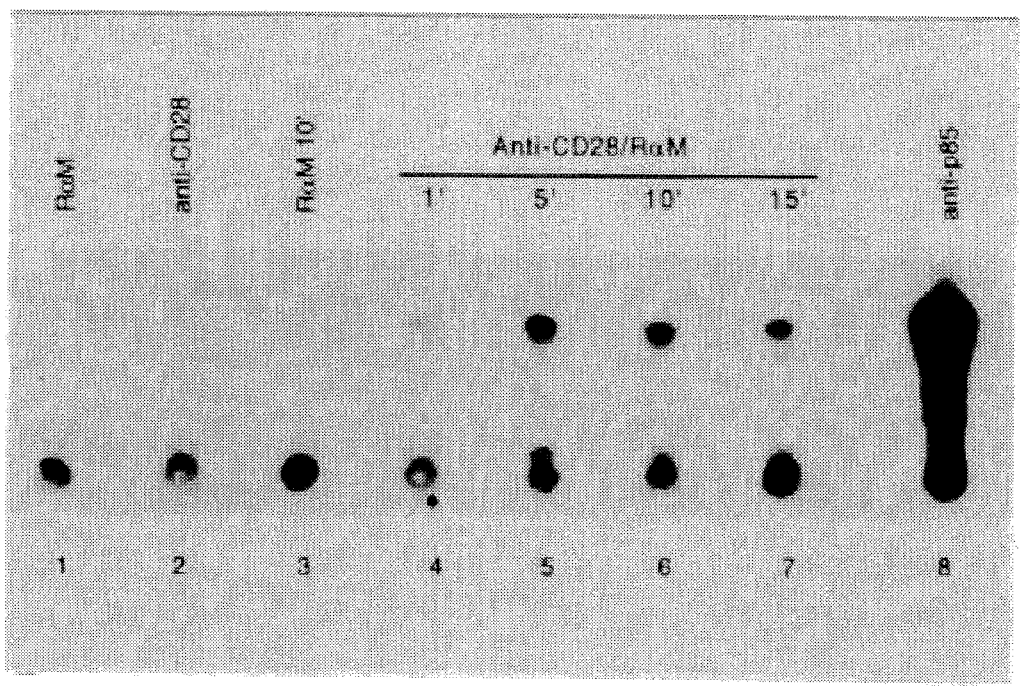
FIG. 4 is a photograph of a thin layer chromatographic analysis of lipids generated by CD28-associated lipid kinase activity following anti-CD28 crosslinking. Jurkat cells were exposed to anti-CD28 antibody and rabbit anti-mouse antibodies for various times, followed by solubilization in NP-40 based lysis buffer, immunoprecipitation and labelling in a lipid kinase assay. Precipitations from untreated cells are shown in lanes 1, 2 and 8. Anti-CD28 crosslinked cells are shown in lanes 4–7. Untreated cells: rabbit anti-mouse immunoglobulin (RαM) (lane 1), anti-CD28 (lane 2) and anti-p85 (lane 8). Anti-CD28 crosslinked samples were analyzed for CD28-associated PI kinase activity after 1 min (lane 4), 5 min (lane 5), 10 min (lane 6) and 15 min (lane 7). RαM crosslinked cells: RαM (lane 3). Immunoprecipitation with anti-p85 served as a positive control (lane 8).
Figure 5:
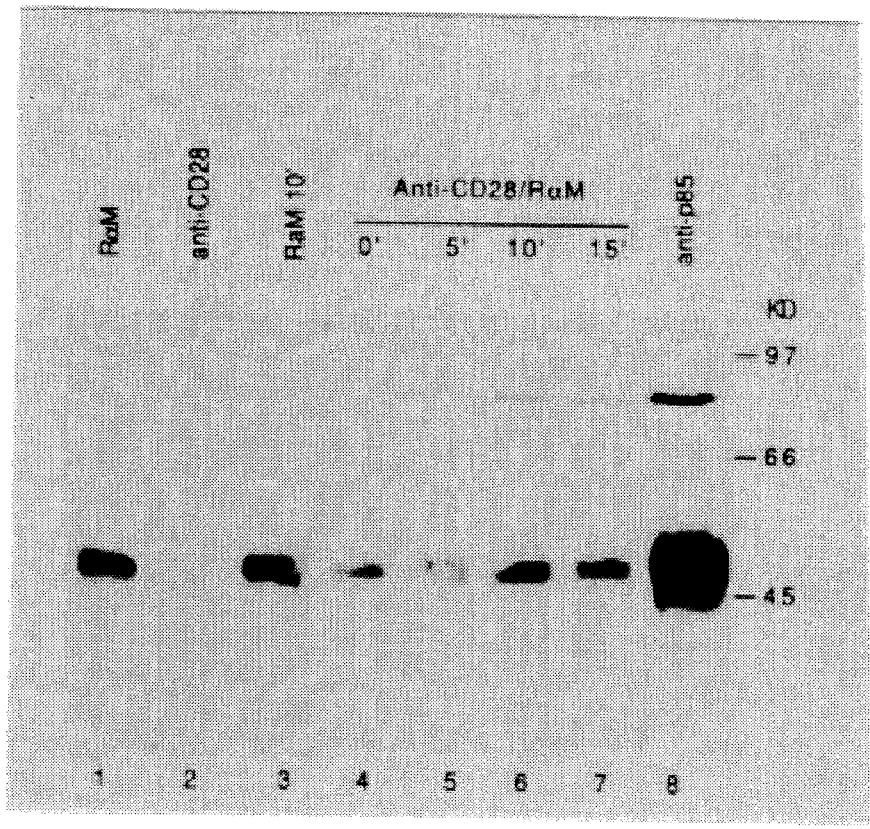
FIG. 5 is a photograph of an immunoblot assay. Jurkat cells were subjected to anti-CD28 cross-linking for various times, followed by solubilization in NP-40 based lysis buffer, immunoprecipitation and immunoblotting with anti-p85 sera. Precipitations from untreated cells are shown in lanes 1,2,8 and precipitations from anti-CD28 crosslinked cells are shown in lanes 4–7. Untreated cells: RαM (lane 1), anti-CD28 (lane 2), and anti-p85 (lane 8). Anti-CD28 crosslinked cells: 0 min (lane 4), 5 min (line 5), 10 min (lane 6), and 15 min (lane 7). RαM crosslinked cells: RαM (lane 3). Immunoprecipitation with anti-p85 antibody served as a positive control (lane 8).
Figure 6:
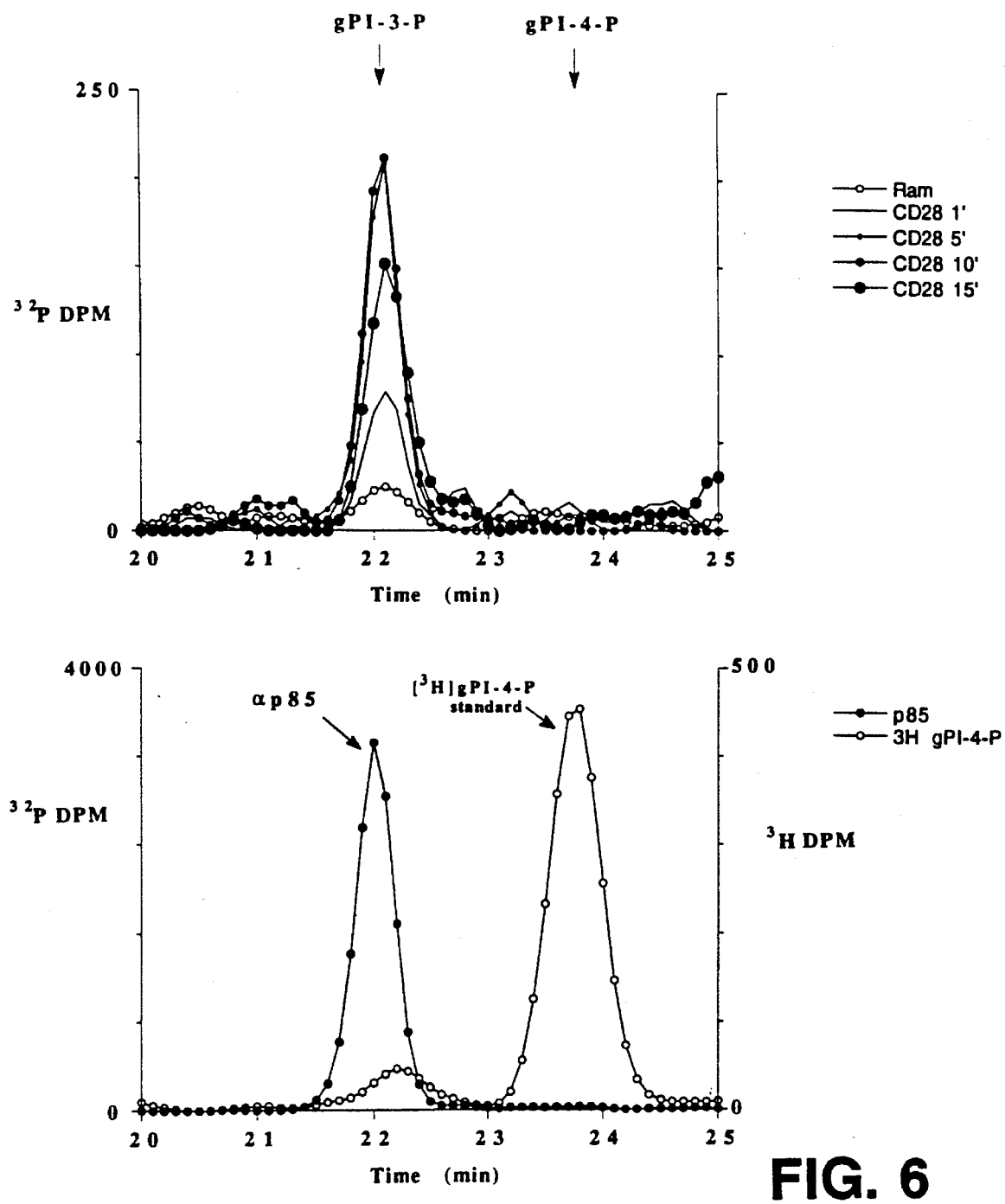
FIG. 6 is a graph showing HPLC analysis of lipid products. PI-P spots were extracted from TLC, deacylated, and subjected to HPLC analysis. Upper panel: HPLC analysis of the eluted PI-P spots showed a 5–8 increase in PI 3-kinase activity. Activity levels reached a plateau at 10 min followed by a slight decrease by 15 min. No other lipid kinase activity was present. PI-P generated in anti-CD28 precipitate was primarily PI 3-P. Lower panel: p85 served as a positive control for PI 3-P (●—●), while $^3$H-PI-4P served as an internal standard for PI 4-P (o—o).

Regulation of PI 3-kinase association with CD28 induced by ligation of cell surface CD28 was evaluated. As seen in FIG. 4, anti-CD28 ligation resulted in a significant increase in the level of PI 3-kinase activity precipitated by an anti-CD28 antibody. An increase in activity was noted as early as 1 min after anti-CD28 ligation (compare lane 4 to lane 2), followed by maximal binding by 5 to 10 min (lanes 5 and 6). A decrease was usually observed by 15 min of ligation (lane 7). Anti-CD28 crosslinking followed by immunoblotting with anti-p85 antibody also showed a dramatic recruitment of the p85 subunit to CD28 (FIG. 5, lanes 5–8). Maximal binding was observed by 10 min, with a slight decrease by 15 min (lanes 7 and 8). Levels of activity reached a plateau at 10 min followed by a slight decrease by 15 min. No other lipid kinase activity was present. These data indicate that CD28 ligation results in the active recruitment of PI 3-kinase to the CD28 antigen. HPLC analysis of the eluted PI-P spots showed a 5–8-fold increase in PI 3-kinase activity (FIG. 6).

Peptide inhibition of CD28/PI 3-kinase association

Figure 7:
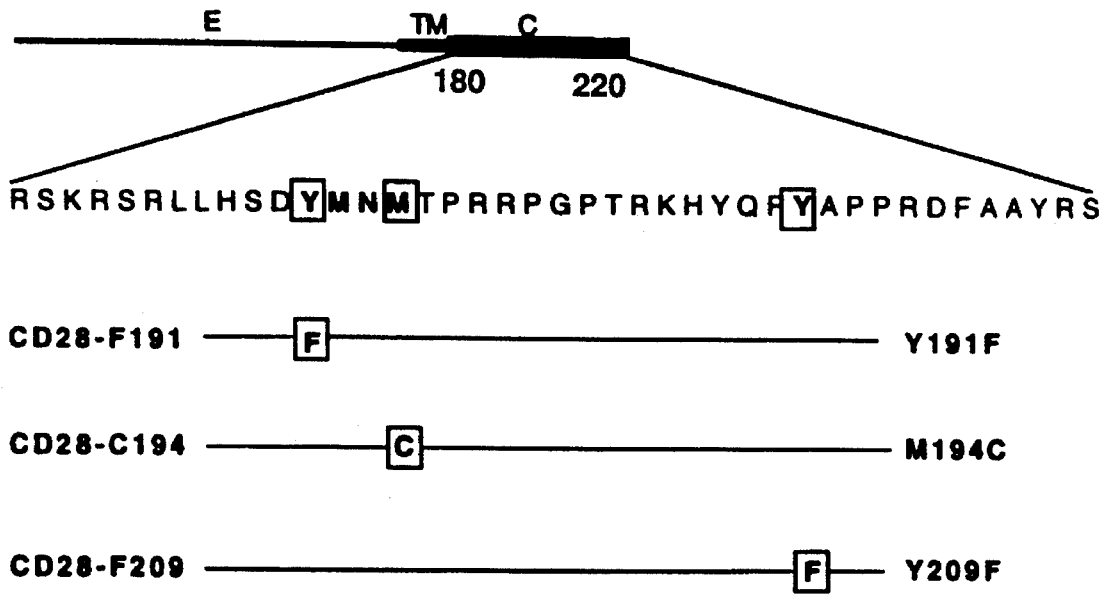
FIG. 7 is a diagram of the CD28 antigen including the extracellular region (E), transmembrane region (TM), and cytoplasmic region (C). Residues 180 to 221 represent the cytoplasmic tail and include the Tyr-Met-X-Met motif (residues 191 to 194) and Tyr (residue 209). Tyr residue at position 191 was mutated to Phe, Met at position 204 to Cys, and Tyr at position 209 to Phe by site-directed mutagenesis.

The cytoplasmic tail of CD28 contains an amino acid sequence fitting the motif, Tyr-Met-X-Met (SEQ ID NO:1), found in other receptors that bind to PI 3-kinase (see Table 1 and FIG. 7). This motif is the optimal binding motif for the SH2 domain of PI 3-kinase found in a variety of other receptors and intracellular proteins, including the platelet-derived growth factor receptor (PDGF-R), colony stimulating factor-1 receptor (CSF-1-R), the Polyoma virus middle T antigen and the IRS-1.

Figure 8:
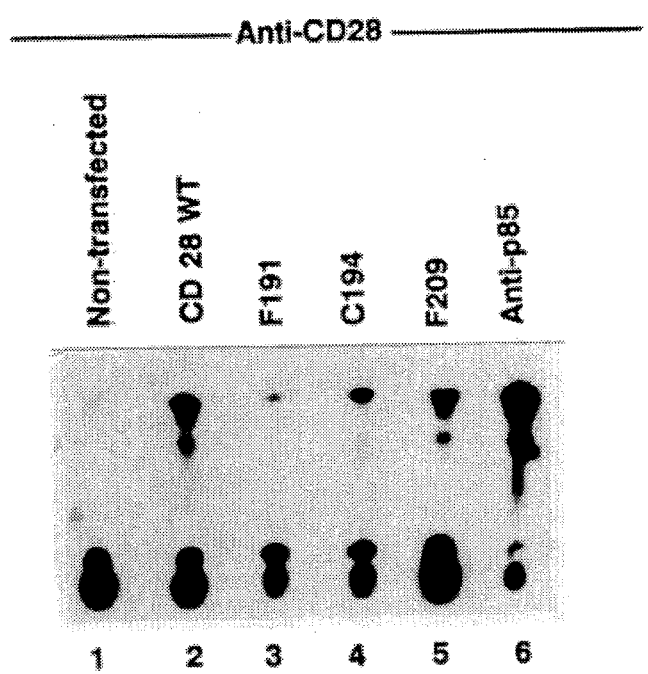
FIG. 8 is a photograph of TLC analysis of lipid products following CD28 crosslinking. Cos-1 cells were transfected with wild type CD28 (WT) (lane 2), Tyr-191 to Phe mutant (F191) (lane 3), Met-194 to Cys (C194) (lane 4), and Tyr-209 to Phe (F209) (lane 5). Transfected cells were then subjected to anti-CD28 crosslinking, immunoprecipitation and lipid kinase analysis. Non-transfected cells served as a negative control (lane 1), while immunoprecipitation with anti-p85 antibody served as a positive control (lane 6).

To directly assess whether PI 3-kinase bound to the motif, CD28 was mutated as described above and assayed for associated PI 3-kinase activity as shown in FIG. 8. As a control, a more distal residue, Tyr-209, was mutated to a Phe residue (F209). Mutation of Tyr-191 resulted in a dramatic decrease in associated PI 3-kinase (compare lane 3 to lane 2). In contrast, mutation of the distal Tyr residue at position 209, F209, had no effect relative to the wild type control (compare lane 5 to lane 2). Mutation of Met-194 within the Tyr-Met-X-Met motif had a partial effect in reducing the level of associated kinase (compare lane 4 to lane 2). The CD28 mutants were expressed at equivalent levels on the cell surface of transfected Cos cells, as detected by FACS analysis.

Figure 9:
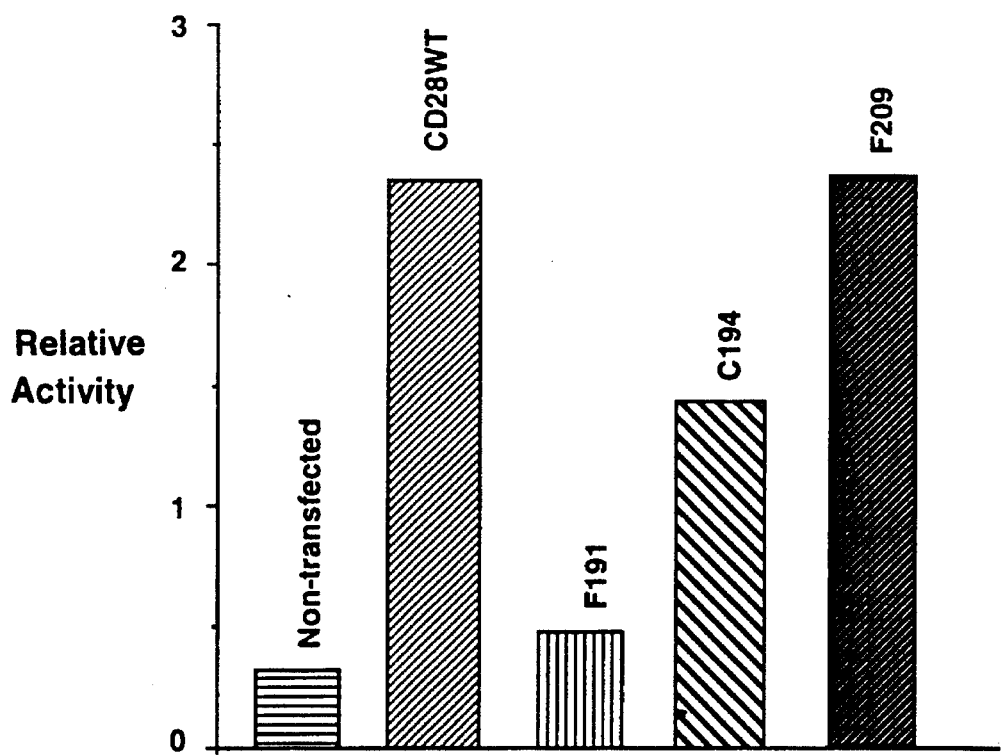
FIG. 9 is a bar graph showing relative autoradiographic intensities of PI-P spots detected in the TLC analysis shown in FIG. 8. Intensity was quantitated by laser densitometric scanning.

The intensity of the spots seen in FIG. 8 was quantitated using laser densitometry. A bar graph showing that analysis is shown in FIG. 9. The F191 mutation effectively reduced the level of PI 3-kinase activity to a level marginally above background, while the C194 mutation partially reduced associated activity (by approximately 40%).

Figure 10:
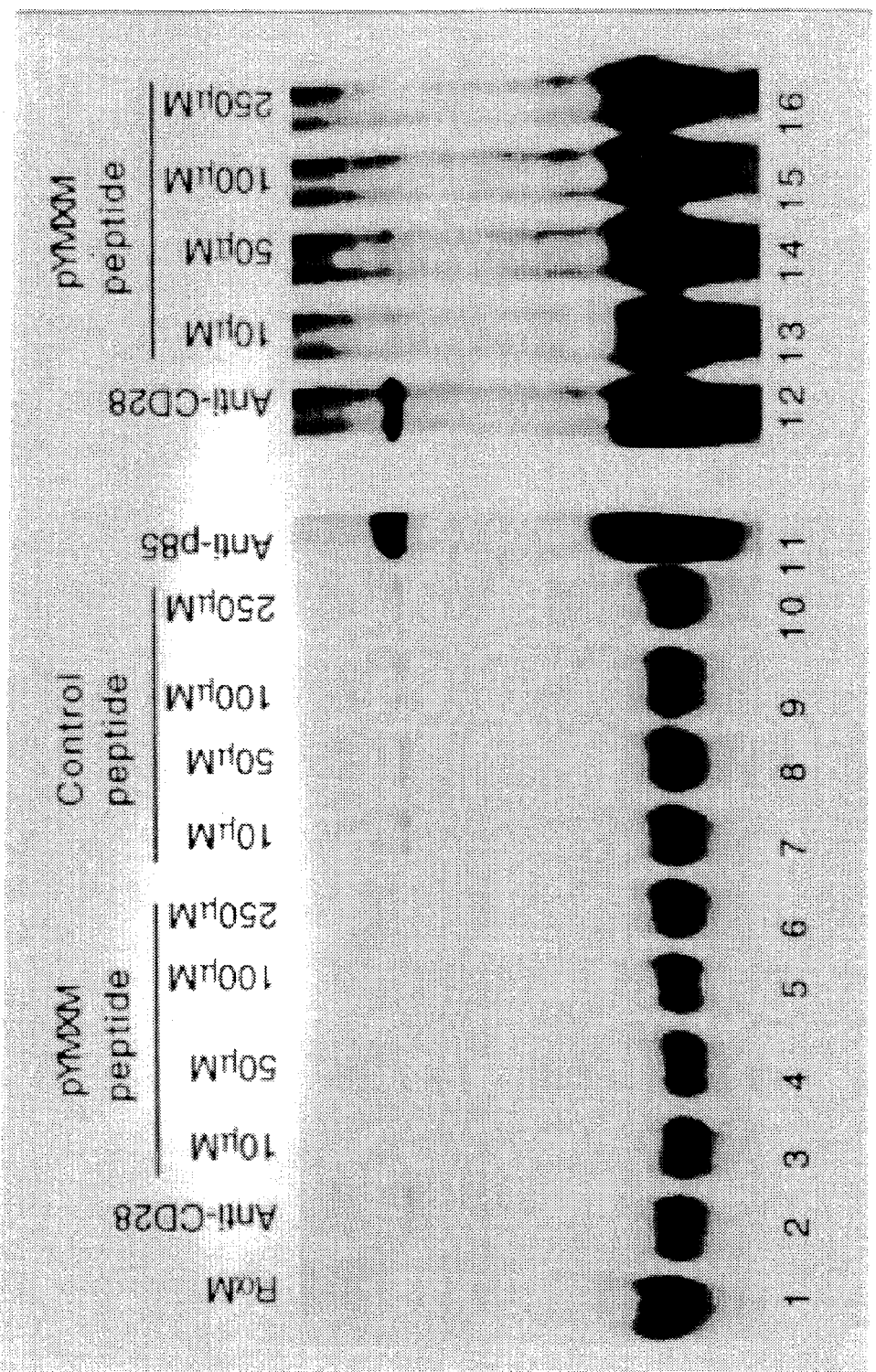
FIG. 10 is a photograph of an immunoblot assay using anti-p85 antibody. Peptides possessing the Tyr-Met-X-Met motif, in which the Tyr residue is phosphorylated, effectively displaced PI 3-kinase from the CD28 antigen as monitored by anti-p85 immunoblotting: RαM (lane 1); anti-CD28 control (lane 2); concentrations of phosphorylated peptide: 10 μM (lane 3), 50 μM (lane 4), 100 μM (lane 5), 250 μM (lane 6); concentrations of non-phosphorylated peptides: 10 μM (lane 7), 50 μM (lane 8), 100 μM (lane 9), 250 μM (lane 10) and anti-p85 control (lane 11). Longer time exposure of autoradiograph showing the effects of various concentrations of phosphorylated peptides: 10 μM (lane 13), 50 μM (lane 14), 100 μM (lane 15) and 250 μM (lane 16). Anti-CD28 control is shown in lane 12.

Similarly, peptides containing the Tyr-Met-X-Met motif with a phosphorylated Tyr residue effectively displaced PI 3-kinase from CD28, as shown in FIG. 10. T cell lysates, exposed to various concentrations of Polyoma-middle T antigen-derived peptide (SEQ ID NO:14) for 2 hours, were subjected to immunoprecipitation with anti-CD28 antibody followed by immunoblotting with anti-p85 antibody. Under these conditions, the phosphorylated peptide effectively displaced PI 3-kinase from CD28 at concentrations as low as 10 μM (compare lanes 3,4,5, and 6 to lane 2). Longer exposures demonstrated that peptide concentrations of 10–50 μM effectively reduced the level of CD28-associated p85 PI 3-kinase by 60–80%, with greater effects seen at 100–250 μM (see lanes 12 through 16). A non-phosphorylated version of the same peptide failed to displace PI 3-kinase, indicating a strict dependency of PI 3-kinase on tyrosine phosphorylation (see lanes 1 through 10). Similarly, phosphorylated CD28-derived peptide (SEQ ID NO:15) blocked the association of PI 3-kinase with CD28, whereas the non-phosphorylated peptide failed to block the association. Scrambled peptides also failed to have an effect on the association of PI 3-kinase with CD28 (data not shown).

Co-stimulation of T cells via CD28

CD28 plays a obligatory co-stimulatory role in the generation of signals transduced by engagement of CD4 and TcRζ/CD3 complex. As described herein, CD28 has been shown to interact directly with the lipid kinase PI 3-kinase, an enzyme common to a number of non-lymphoid receptors that control cell growth. Furthermore, ligation of CD28 was observed to result in a dramatic increase in the level of PI 3-kinase activity, and recruitment of the p85 subunit to the receptor. Both observations are consistent with a role for PI 3-kinase in mediating the crucial second signal required for the proliferation of T-cells. The first signal is initiated by ligation of CD4/CDS-TcRζ/CD3, an event mediated by src-kinases such as $p56^{lck}$, $p59^{fyn}$, modified $p72^{fyn}$ and ZAP-70 that can interact with surface receptors such as CD4, CD8 and the TcRζ/CD3 complex (Rudd et al., 1988, Proc. Natl. Acad. Sci. USA 85:5190; Samelson et al., 1991, Proc. Natl. Acad. Sci. USA 87:4358; Chan et al., 1992, Proc. Natl. Acad. Sci. USA 89:9166).

CD28 is now known to be one of several proteins which lack endogenous tyrosine kinase activity, and which bind to PI 3-kinase. Others include middle T antigen of Polyoma virus, the insulin IRS protein, and the CD19 antigen, each of which possess a Tyr-Met-X-Met motif. The CD28-PI 3-kinase association provides an alternative mechanism by which the T-cell receptors may interact directly with PI 3-kinase, in contrast to the interaction of the CD4-$p56^{lck}$ and TcRζ/CD3-$p59^{fyn}$ with PI 3-kinase which is mediated by the SH3 domain of the tyrosine kinase. Thus, CD28 binding to PI 3-kinase differs from the mechanism used by src kinases in recruiting the enzyme. Furthermore, the level of PI 3-kinase activity associated with src kinases is much lower than that associated with CD28. Thus, the mechanism of recruiting and binding PI 3-kinase utilized by the CD4-$p56^{lck}$ and TcRζ/CD3-$p59^{fyn}$ complexes differs fundamentally from that utilized by CD28, and the PDGF, insulin, and CSF-1 receptors.

CD28 signalling is resistant to a variety of reagents including cholera toxin, cyclosporine A and FK506 (June et al., supra). Cholera toxin inhibits the function of G proteins, while cyclosporine A and FK506 inhibit signalling by cyclophilins and calcineurin. CD28-mediated signalling via PI 3-kinase is therefore likely to operate independent of the G proteins and the cyclophilin/calcineurin pathway.

Use

The absence of the second signal in T cells results in unresponsiveness or anergy. Anergy and tolerance appear to play roles in autoimmunity and in the recognition of tumors (Townsend et al., 1993, Science 259:368; Chen et al., 1992, Cell 71:1093). Dysregulation of the second signal may also result in certain disease states.

The importance of uncovering the signalling mechanism of CD28 in T cells is underlined by its importance in immunotherapy against tumor cells, and in autoimmunity. The generation of CD8+ cytotoxic T cells against tumors is greatly amplified by the expression of B7 in target cells. For example, melanoma cells, normally resistant to cytotoxic killing, are killed when transfected with the CD28 ligand, B7 (Chen et al., supra). Similarly, B7 expression on Langerhans cells induces T-cell infiltration, MHC class II recognition and diabetes in transgenic mice. The mechanism involves the direct activation of CD8+ cells via IL-2, and can be blocked by anti-B7 antibody binding to the B7 ligand, CD28. Stimulation of PI 3-kinase activity through the B7/CD28 signalling mechanism is the likely intracellular messenger responsible for the enhanced generation of cytotoxic T cells and/or their eventual effector mechanisms. Reagents that block PI 3-kinase or its downstream targets would prove valuable therapeutic tools.

Since blocking the association of PI 3-kinase with CD28 can interfere with activation of T cells, this method may be useful in downregulating the immune response in patients with autoimmune diseases such as systemic lupus erythematosus (SLE), type 1 diabetes, and rheumatoid arthritis. Suppression of the T cell-mediated immune response using this method may also be useful in the treatment of allograft or xenograft recipients to prevent rejection of a transplanted organ or cells.

Since stimulation of PI 3-kinase activity is the likely intracellular messenger responsible for the enhanced generation of cytotoxic T cells described above, the immune response can be therapeutically augmented by providing multiple copies of a PI 3-kinase binding sequence in the cytoplasmic tail of a T cell co-stimulatory protein. Crosslinking of modified T cell surface proteins could induce binding of PI 3-kinase to each of the binding sequences present in the cytoplasmic tail of the costimulatory protein, resulting in amplification of the signal transduced and thus, amplification of T cell activation. Activation of cytotoxic T cells in this manner can be used to boost the immune response against tumor cells following surgery or in conjunction with other cancer therapies. The T cells of immunocompromised or immunosuppressed patients can be similarly activated.

EXAMPLE 1

Blocking signal transduction in T cells

Peptide sequences that can be used to block the association of PI 3-kinase with CD28 include peptides having the sequence of SEQ ID NO: 1 as well as other PI 3-kinase binding sequences (see Table 1). Other such sequences can be readily identified by scanning the amino acid sequences of other signal transduction and receptor proteins for regions homologous to SEQ ID NO:1. Polypeptide fragments of signal transduction or receptor proteins can be made using methods well known in the art, such as standard recombinant DNA techniques or proteolytic cleavage of full-length proteins. Preferably, synthetic peptides of various lengths can be made according to standard methods using a peptide synthesizer. Screening of polypeptide fragments or synthetic peptides for T cell modulating activity can be accomplished using the screening methods of the invention, as described below.

Since the cytoplasmic domain of CD28 includes approximately 50 amino acids, a polypeptide useful for blocking the interaction of PI 3-kinase with CD28 will ordinarily be at least about 4 amino acids (e.g., 8 amino acids), usually about 10 contiguous amino acids, preferably at least 20 contiguous amino acids, and most preferably at least 40 or 50 amino acids in length.

TABLE 1

| CD28 | LHSD | YMNN | TPRRP | SEQ ID NO:2 |
| PDGF-R | SDGG | YXDM | SKDES | SEQ ID NO:3 |
| CSF-1 R | GVDT | YVEM | RP | SEQ ID NO:4 |
| c-KIT | STNE | YMDM | KP | SEQ ID NO:5 |
| IRS-1 | DDG | YMPM | SPGV | SEQ ID NO:6 |
| IRS-1 | GNGD | YMPM | SPKS | SEQ ID NO:7 |
| IRS-1 | PNG | YMMM | SPSG | SEQ ID NO:8 |
| IRS-1 | TGD | YMNM | SPVG | SEQ ID NO:9 |
| IRS-1 | SEE | YMNM | DLGP | SEQ ID NO:10 |
| Polyoma | EEEE | YMPM | EDLYL | SEQ ID NO:11 |
| EGF-R | DADE | YLIP | QQGFF | SEQ ID NO:12 |
| FGF-R | SNQE | YLDL | SMPLD | SEQ ID NO:13 |

Introduction of such polypeptides into the cytoplasm of T cells blocks signal transduction by inhibiting the binding of PI 3-kinase to the PI 3-kinase binding sequence in the cytoplasmic domain of CD28, thus effectively stopping the transduction of a surface-generated signal and decreasing T cell activation.

Modified CD28 lacking a portion of the cytoplasmic tail, which portion includes the segment Tyr-Met-Asn-Met (SEQ ID NO:16), or comprising at least one deletion or mutation in this segment of the tail, decreases binding of PI 3-kinase to CD28, resulting in a decrease in T cell activation. Introduction of such molecules into T cells can be used to decrease T cell activation, because without the ability to bind PI 3-kinase, the surface ligation of such molecules would be incapable of transducing a cytoplasmic signal.

TABLE 2

| | |
|---|---|
| YMNM | SEQ ID NO:16 |
| YMDM | SEQ ID NO:17 |
| YVEM | SEQ ID NO:18 |
| YMPM | SEQ ID NO:19 |
| YLIP | SEQ ID NO:20 |
| YLDL | SEQ ID NO:21 |

Proteins or peptides may be administered to the patient intravenously in a pharmaceutically acceptable carrier such as physiological saline. Since these peptides must act in the cytoplasm of the cell, standard methods for intracellular delivery of peptides can be used, e.g. via liposomes. Such methods are well known to those of ordinary skill in the art. It is expected that an intravenous dosage of approximately 1 to 1000 μmoles of the peptide of the invention would be administered per kg of body weight per day to achieve an effective concentration within the cytoplasm of the T cell. The formulations of this invention are useful for parenteral administration, such as intravenous, subcutaneous, intramuscular, and intraperitoneal delivery routes.

In addition to systemic administration of peptides, peripheral blood can be taken from a patient, and the T cells purified and allowed to take up proteins or peptides of the invention, e.g., by fusion with protein-loaded liposomes; the treated T cells are then reintroduced into the patient's bloodstream.

Also included in the invention is a method of treating an allograft, e.g. an organ such as a kidney or liver, by perfusing, soaking, or electroporating the organ with solution containing the proteins or peptides of the invention prior to transplantation. Immunocompetent T cells in the treated organ would be suppressed, thus blocking the development of graft versus host disease in the transplant recipient.

EXAMPLE 2

Augmenting signal transduction in T cells

To enhance or increase T cell activation, T cell surface proteins such as CD28, CD2, CD3, CD7, CTLA-4, LFA-1, CD18, CD5, CD4, or CDS, engineered to contain a plurality of PI 3-kinase binding domains in their cytoplasmic tails, can be introduced into T cells.

Such proteins can be produced recombinantly. DNA encoding the modified proteins can be made using standard recombinant techniques. A DNA fragment, generated by restriction enzyme digestion or de novo synthesis and encoding the PI 3-kinase binding domains, can be introduced into DNA encoding the cytoplasmic tail of the T cell surface protein. The DNA can then be ligated into an expression vector, and the vector introduced into a procaryotic or eucaryotic cell, e.g., Sf21 cells for baculoviral expression. The protein can then be purified using standard techniques, such as gel filtration, ion exchange chromatography or affinity chromatography, e.g., immunoaffinity chromatography using an antibody specific for the modified protein. The proteins can then be packaged into liposomes using methods known in the art. Since liposomes are able to fuse with the lipid membranes of cells, the contents of the liposomes can thus be delivered to the cells of interest, i.e., T cells.

Proteins modified as described above and introduced into T cells can augment T cell activation by providing additional sites for PI 3-kinase binding. Such modified surface proteins could potentiate a greater intracellular signal than unmodified T cells, resulting in augmented activation of T cell function. For example, in some disease states, such as cancer, in which the T cells of a patient may be anergic or suppressed, the invention could be used to activate or hyper-activate cytotoxic T cells to kill unwanted cells, such as tumor cells or cells infected with a pathogenic virus.

Also within the invention are analogues of the above proteins and peptides. Analogues can differ from the native peptides by amino acid sequence, or by modifications which do not affect the sequence, or by both. Modifications (which do not normally alter primary sequence) include in vivo or in vitro chemical derivitization of polypeptides, e.g., acetylation or carboxylation of the termini.

Since the extracellular domain of CD28 contains several potential sites for glycosylation, the proteins and polypeptides of the invention may be glycosylated or unglycosylated. Similarly, various amino acids may be phosphorylated, e.g., phosphotyrosine, phosphoserine, or phosphothreonine.

The invention includes analogues in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue with its R-isomer is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

EXAMPLE 3

Gene Therapy

Also within the invention are isolated nucleic acid sequences that encode the peptides described above. For blocking or augmentation of T cell activation, the peptides and proteins described above must be delivered to the cytoplasm of the cell. Using gene therapy techniques, DNA encoding the proteins and peptides of the invention is taken up by cells and expressed in the cytoplasm.

The DNA of the invention has been purified from the sequences which flank it in a naturally occurring state, e.g., a DNA fragment which has been removed from the sequences which are normally adjacent to the fragment, e.g., the sequences adjacent to the fragment in a genome in which it naturally occurs. In some cases, the DNA has been modified by the addition of DNA fragments encoding the PI 3-kinase binding site. Such fragments can be generated by restriction enzyme digestion or de novo synthesis and can be introduced into the DNA encoding the cytoplasmic tail of PI 3-kinase using genetic engineering methods well known in the art. Alternatively, utilizing the known DNA sequences of T cell surface proteins, such as CD28 (Aruffo et al., supra), CD3 (Clevers et al., 1988, Ann. Rev. Immunol., pp. 629–662), CD7 (Aruffo et al., 1987, The EMBO J. 6:3313–3316, 1987) and CTLA-4 (Daviavach et al., 1988, Eur. J. Immunol. 18:1901–1905), DNA encoding the modified proteins of the invention can be generated using PCR. The DNA can also be synthetically generated using an oligonucleotide synthesizer. The DNA can then be incorporated into a vector; into an autonomously replicating plasmid or virus; or into the genomic DNA of a prokaryote or eucaryote.

The DNA of the invention may be introduced into target cells in the bloodstream or other tissues of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

Also included is a method of treating an allograft, e.g. an organ such as a kidney or liver, by perfusing, soaking, or electroporating the organ with solution containing a nucleic acid sequence encoding a peptide fragment of the cytoplasmic domain of CD28, such as SEQ ID NO:1 prior to transplantation. Immunocompetent T cells in the treated organ would be suppressed, thus blocking the development of graft versus host disease in the transplant recipient.

The invention also includes cells transfected with the DNA of the invention. Standard methods for transfecting cells with isolated nucleic acid are well known to those skilled in the art of molecular biology. Cells can be taken from the bloodstream or tumor site of a patient, transfected ex vivo, and returned to the patient. Preferably, the cells are T cells, and they express a peptide or genetically engineered protein of the invention encoded by the nucleic acid of the invention upon return to the patient.

A therapeutic composition is provided which includes a pharmaceutically acceptable carrier and a therapeutically effective amount of a nucleic acid, wherein the nucleic acid includes a promoter operatively linked to a sequence encoding a heterologous polypeptide, to generate high-level expression of the polypeptide in T cells transfected with the nucleic acid. The promoter may be selected from those which preferentially direct expression of proteins in T cells, such as the $p56^{lck}$ promoter or the CD3 promoter. The therapeutic composition may also include a gene delivery system as described above. Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately 106 to 1022 copies of the nucleic acid molecule.

EXAMPLE 4

Screens for therapeutically useful modulators

A screening method for identifying compounds capable of modulating the association of PI 3-kinase with CD28 can be carried out as follows:

The assay utilizes a cell that expresses PI 3-kinase and CD28. The cell is most preferably a T cell such as HPB-ALL or Jurkat, but may be any type of cell which expresses CD28 on its surface and PI 3-kinase in its cytoplasm, e.g., a cell transfected with cDNAs encoding CD28 and/or PI 3-kinase. A sample of cells is incubated in the presence or in the absence of a candidate compound. A reference point could be established under standard conditions and the results from any assay compared to the pre-established standard as the control. Alternatively, controls could be run in parallel with each screening assay. Cell surface CD28 is cross-linked with, e.g., a CD28-specific antibody or a CD28 ligand, such as B7. The CD28-PI 3-kinase-complex is immunoprecipitated with Protein A Sepharose beads, subjected to SDS-PAGE under denaturing conditions, and immunoblotted with antibody specific for PI 3-kinase, e.g., an anti-p85 antibody. A reduction of the amount of protein on the immunoblot compared to a standard or to a control immunoblot carried out in the absence of a candidate compound, indicates inhibition of association of PI 3-kinase with CD28. The intensity of staining can be quantitated by means of standard densitometric techniques.

In a variation of the assay described above, cells which express CD28 on the cell surface and PI 3-kinase in the cytoplasm can be incubated in the presence and absence of a candidate compound, and the association of CD28 with PI 3-kinase evaluated by lysing the cells, immunoprecipitating PI 3-kinase with an anti-PI 3-kinase antibody such as anti-p85, and determining the amount of CD28 in the immunoprecipitate using, e.g., a CD28-specific antibody in a quantitative technique such as ELISA.

A method which measures the inhibition of PI 3-kinase activity by a given compound can also be used to identify compounds capable of modulating T cell activation. Using cells which express CD28 and PI 3-kinase, cell surface CD28 is crosslinked and immunoprecipitated as described above. The immunoprecipitated complex is assayed for lipid kinase activity using phosphatidyl inositol and $\gamma 32P$-ATP, as described above. Following the reaction, lipids are extracted, separated using TLC, and visualized using autoradiography. A reduction in amount of 32P-labeled PI-3P detected on the chromatographic plate, compared to the amount observed in a control sample which was not exposed to the candidate compound, indicates that the candidate compound inhibits the association of PI 3-kinase with CD28. The candidate compounds can thus be evaluated with respect to their ability to reduce the amount of precipitable PI-3P in a test sample compared to a standard or control sample carried out in the absence of the candidate compounds.

The association of CD28 with PI 3-kinase can also be measured in an in vitro assay, by contacting CD28 and/or the p85 subunit PI 3-kinase with a candidate compound, either individually or simultaneously. To detect complex formation, one of the components, e.g., CD28, is labelled prior to exposure to the candidate compound, the complex immunoprecipitated with an antibody to the second component, e.g., p85, and the amount of radioactivity in the immunoprecipitate measured. For example, iodinated CD28, derived from lactoperoxidase-labelled cells, associated with p85 can be immunoprecipitated with p85-specific antibodies. A reduction in the amount of immunoprecipitated radioactivity in the presence of a candidate compound indicates that the compound inhibits the interaction of PI 3-kinase with CD28 and is likely to modulate T cell activation.

EXAMPLE 5

Transgenic Mice

Transgenic mice can be made by standard methods, e.g., as described in Leder et al., U.S. Pat. No. 4,736,866, herein incorporated by reference.

Briefly, one would prepare a vector containing a CD28 cDNA modified to encode multiple (e.g., 2–10) copies of the PI 3-kinase binding motif, SEQ ID NO:1, within the cytoplasmic tail of the protein. These multiple copies may be adjacent to each other or may be separated from each other by one or more residues to ensure that binding of multiple molecules of PI 3-kinase is not sterically hindered.

In one example, the vector would have the proximal promoter element of a T cell-specific promoter, e.g., $p56^{lck}$ promoter, fused to DNA corresponding to the 3' end of coding sequence for the human growth hormone (HGH) gene followed by a polyadenylation site. DNA encoding CD28 modified to contain multiple copies of the Tyr-Met-X-Met motif can be generated using de novo synthesis or PCR, and cloned into a unique BamH1 restriction enzyme site in the vector between the promoter and the HGH coding sequence. The transgene construct containing $p56^{lck}$ promoter sequence, modified CD28 coding sequence, and polyadenylation site can then be excised from the vector using a restriction enzyme, e.g., NotI for the vector described above. Following gel purification, the DNA can be injected into murine zygotes, e.g., C57BL/6J X DBA/2F2 zygotes. Incorporation of the transgene into murine genomic DNA can be monitored using methods well known in the art of molecular biology, e.g., dot blotting tail DNA with a probe complimentary to the 3' region of the human growth hormone gene contained in the transgene construct. Mice thus confirmed to harbor the transgene can then be used as founders. Animal lines can be created by crossing founders with C57BL/6J mice (The Jackson Laboratory, Bar Harbor, Me.).

Other embodiments

Other embodiments are within the following claims.

What is claimed is:

1. A method of modulating signal transduction in T cells, which method comprises introducing into a T cell a peptide which decreases the direct binding of PI 3-kinase to CD28, wherein said peptide comprises a phosphorylated PI 3-kinase-binding-fragment of the cytoplasmic tail of CD28.

2. The method of claim 1, wherein said peptide comprises SEQ ID NO:1, wherein the tyrosine residue of said peptide is phosphorylated.

* * * * *